(12) United States Patent
Mathews et al.

(10) Patent No.: US 12,118,725 B2
(45) Date of Patent: Oct. 15, 2024

(54) ANALYZING IMAGE DATA TO DETERMINE BOWEL PREPARATION QUALITY

(71) Applicant: The Johns Hopkins University, Baltimore, MD (US)

(72) Inventors: Simon C. Mathews, Clarksville, MD (US); Amit Banerjee, Silver Spring, MD (US); Jay Pasricha, Ellicott City, MD (US)

(73) Assignee: The Johns Hopkins University, Baltimore, MD (US)

( * ) Notice: Subject to any disclaimer, the term of this patent is extended or adjusted under 35 U.S.C. 154(b) by 557 days.

(21) Appl. No.: 17/310,686

(22) PCT Filed: Feb. 14, 2020

(86) PCT No.: PCT/US2020/018390
§ 371 (c)(1),
(2) Date: Aug. 17, 2021

(87) PCT Pub. No.: WO2020/172073
PCT Pub. Date: Aug. 27, 2020

(65) Prior Publication Data
US 2022/0076418 A1    Mar. 10, 2022

Related U.S. Application Data
(60) Provisional application No. 62/807,079, filed on Feb. 18, 2019.

(51) Int. Cl.
*G06T 7/00* (2017.01)
*G16H 50/20* (2018.01)
*G16H 50/30* (2018.01)

(52) U.S. Cl.
CPC ........... *G06T 7/0014* (2013.01); *G16H 50/20* (2018.01); *G16H 50/30* (2018.01); *G06T 2207/30004* (2013.01)

(58) Field of Classification Search
CPC ... G06T 2207/3004; G06T 2207/30028; G06T 2207/30032; G16H 50/30
See application file for complete search history.

(56) References Cited

U.S. PATENT DOCUMENTS
9,689,803 B1 * 6/2017 Ruttner ............... H04N 1/3224
2005/0261605 A1 11/2005 Shemer et al.
(Continued)

FOREIGN PATENT DOCUMENTS
JP    2010172498 A    8/2010
JP    2018109597 A    7/2018
(Continued)

OTHER PUBLICATIONS
Anonymous, "Smart Toilet' Uses Artificial Intelligence to Monitor Bowel Health", May 24, 2021, 3 pages, Duke Today, Duke University https://today.duke.edu/2021/05/smart-toilet-uses-artificial-intelligence-monitor-bowel-health.
(Continued)

*Primary Examiner* — Wen W Huang
(74) *Attorney, Agent, or Firm* — Harrity & Harrity, LLP

(57) ABSTRACT

An analyzing platform may obtain a first image of a liquid in a receptacle. The analyzing platform may analyze the first image to determine a first set of visual characteristics concerning the liquid. The analyzing platform may obtain a second image of a rectal sample in the liquid in the receptacle, wherein the rectal sample originated from a bowel of a subject. The analyzing platform may analyze the second image to determine a second set of visual characteristics concerning the rectal sample. The analyzing platform may determine, based on the first set of visual characteristics and the second set of visual characteristics, rectal sample infor-
(Continued)

mation. The analyzing platform may cause one or more actions to be performed based on the rectal sample information.

20 Claims, 9 Drawing Sheets

(56) References Cited

U.S. PATENT DOCUMENTS

| | | | |
|---|---|---|---|
| 2018/0085098 A1* | 3/2018 | Attar | G01N 33/493 |
| 2018/0317800 A1 | 11/2018 | Coleman et al. | |
| 2019/0212322 A1* | 7/2019 | Tsuruoka | A61B 5/6887 |
| 2019/0383793 A1* | 12/2019 | Sugiyama | G01N 35/1009 |

FOREIGN PATENT DOCUMENTS

| | | |
|---|---|---|
| KR | 10-2016-0046933 A | 5/2016 |
| WO | 2018187790 A2 | 10/2018 |

OTHER PUBLICATIONS

Anonymous, "Seed Health Announces Acquisition of Digital Health Company Auggi", Feb. 8, 2021, 3 pages, Seed Health.
International Search Report and Written Opinion for Application No. PCT/US2020/018390, mailed on Jun. 8, 2020, 9 pages.

* cited by examiner

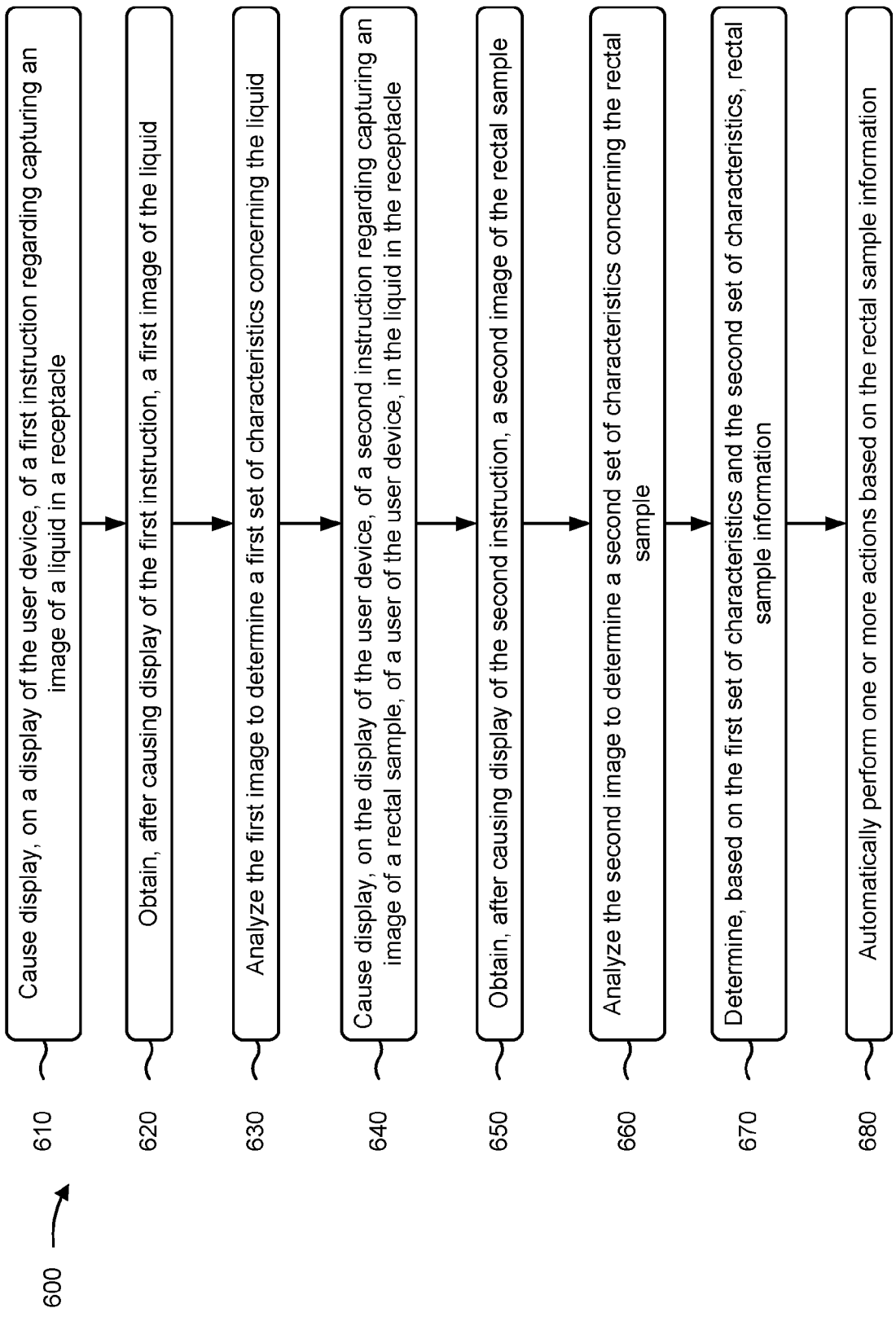

ANALYZING IMAGE DATA TO DETERMINE BOWEL PREPARATION QUALITY

RELATED APPLICATIONS

This application is a 371 national stage of PCT Application No. PCT/US2020/018390 filed on Feb. 14, 2020, entitled "ANALYZING IMAGE DATA TO DETERMINE RECTAL SAMPLE INFORMATION," which claims priority to U.S. Provisional Patent Application No. 62/807,079, filed on Feb. 18, 2019, and entitled "ANALYZING IMAGE DATA TO DETERMINE BOWEL PREPARATION QUALITY", which are incorporated by reference herein in their entireties.

BACKGROUND

A colonoscopy is an endoscopic procedure that is commonly used to screen for colorectal cancer or to detect other abnormalities in the large intestine and rectum. In many cases, a patient consumes a bowel preparation agent to cleanse the bowel before undergoing a colonoscopy. A clean bowel aids an endoscopist's ability to visualize colonic mucosa.

SUMMARY

According to some implementations, a method may include obtaining, by a device, a first image of a liquid in a receptacle; analyzing, by the device, the first image to determine a first set of visual characteristics concerning the liquid; obtaining, by the device, a second image of a rectal sample in the liquid in the receptacle, wherein the rectal sample originated from a bowel of a subject; analyzing, by the device, the second image to determine a second set of visual characteristics concerning the rectal sample; determining, by the device and based on the first set of visual characteristics and the second set of visual characteristics, rectal sample information; and causing, by the device, one or more actions to be performed based on the rectal sample information.

According to some implementations, a device may include one or more memories, and one or more processors, communicatively coupled to the one or more memories, configured to: obtain, from a user device, a first image of a liquid in a receptacle; analyze the first image to determine a characteristic associated with the liquid; obtain, from the user device, a second image of a rectal sample in the liquid in the receptacle; analyze the second image to determine a characteristic associated with the rectal sample; determine, using one or more machine learning models and based on the characteristic associated with the liquid and the characteristic associated with the rectal sample, rectal sample information; and cause one or more actions to be performed based on the rectal sample information.

According to some implementations, a non-transitory computer-readable medium may store one or more instructions. The one or more instructions, when executed by one or more processors of a user device, may cause the one or more processors to: cause display, on a display of the user device, of a first instruction regarding capturing an image of a liquid in a receptacle; obtain, after causing display of the first instruction, a first image of the liquid; analyze the first image to determine a first set of characteristics concerning the liquid; cause display, on the display of the user device, of a second instruction regarding capturing an image of a rectal sample, of a user of the user device, in the liquid in the receptacle; obtain, after causing display of the second instruction, a second image of the rectal sample; analyze the second image to determine a second set of characteristics concerning the rectal sample; determine, based on the first set of characteristics and the second set of characteristics, rectal sample information; and automatically perform one or more actions based on the rectal sample information.

BRIEF DESCRIPTION OF THE DRAWINGS

FIGS. 4-6 are flowcharts of example processes for analyzing image data to determine rectal sample information.

DETAILED DESCRIPTION

Figure 1A:
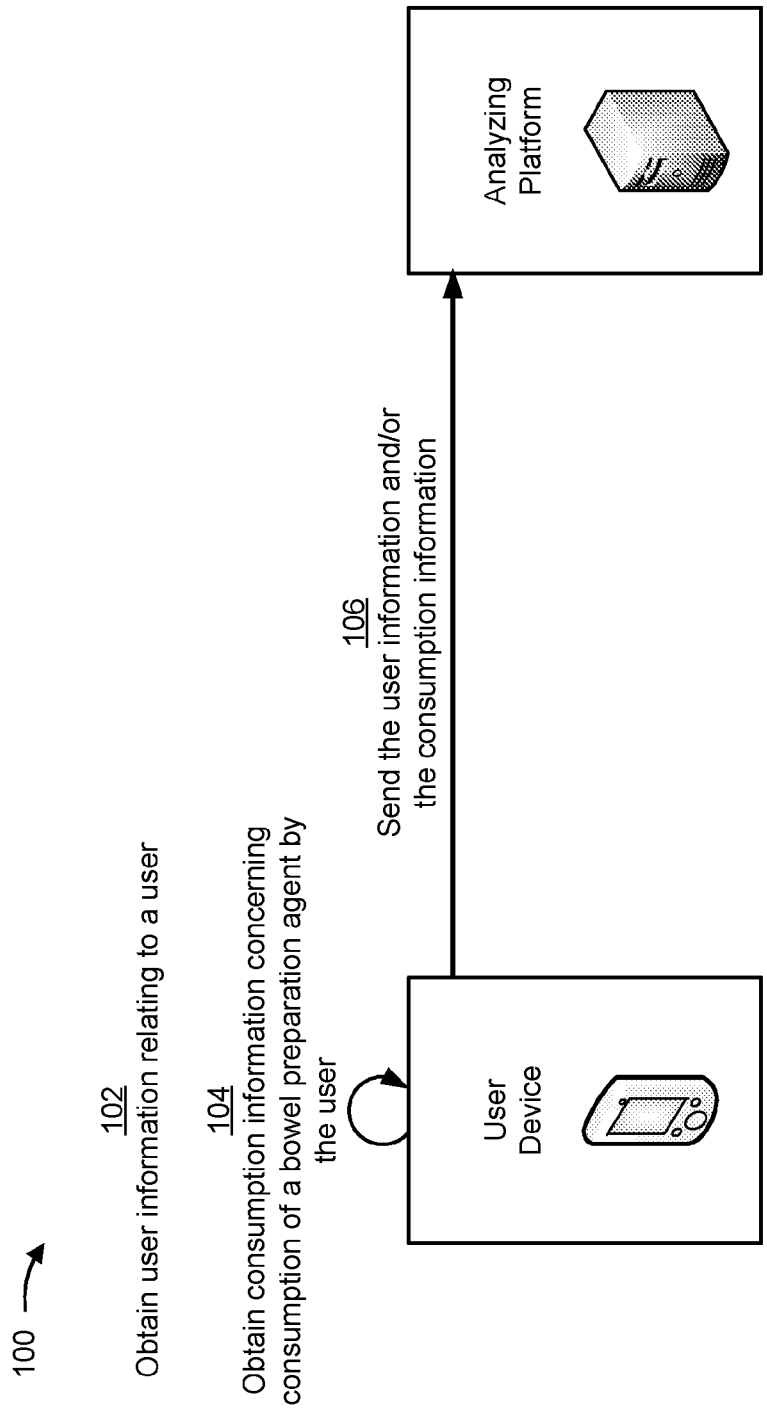
FIGS. 1A-1D are diagrams of example implementations described herein.

The following detailed description of example implementations refers to the accompanying drawings. The same reference numbers in different drawings may identify the same or similar elements.

A colonoscopy is an endoscopic procedure commonly used to screen for colorectal cancer or to detect other abnormalities in the colon of a patient. In many cases, a patient consumes a bowel preparation agent to cleanse the patient's bowel before undergoing a colonoscopy. A clean bowel aids an endoscopist's ability to visualize colonic mucosa while performing the colonoscopy. A predictor of colonoscopy quality (e.g., whether the endoscopist is able to identify and diagnose lesions in the bowel) is the quality of bowel preparation (e.g., how well bowel is cleaned so that colonic mucosa can be visualized). In some cases, the quality of bowel preparation is poor (e.g., the bowel is not sufficiently clean for the endoscopist to visualize the colonic mucosa). In such cases, the colonoscopy is considered inadequate and commonly results in longer procedure time, increased risk to patients, decreased quality, and/or an incomplete examination. As a result, the procedure frequently needs to be repeated.

This may unnecessarily consume resources associated with scheduling and performing the colonoscopy. For example, a device associated with scheduling colonoscopy appointments unnecessarily uses resources (e.g., processing resources, memory resources, power resources, communication resources, and/or the like) to schedule an additional colonoscopy at a later time. Further, resources (e.g., processing resources, memory resources, communication resources, and/or the like) associated with facilitating imaging of the patient's colon may be unnecessarily used for a colonoscopy that needs to be redone. Moreover, resources may be unnecessarily used to facilitate cleaning and sterilizing of colonoscopy tools and equipment (e.g., a colonoscope, cleaning solution, tubing, and/or the like) for a colonoscopy that needs to be redone.

According to some implementations described herein, a user device and/or an analyzing platform obtains a first image of a liquid in a receptacle (e.g., water in a toilet) and analyzes the first image to determine a first set of visual characteristics concerning the liquid. In some implementations, the user device and/or analyzing platform obtains a second image of a rectal sample (e.g., of the user) in the liquid in the receptacle (e.g., a rectal effluent, a rectal discharge, stool, and/or the like in the water in the toilet) and analyzes the second image to determine a second set of visual characteristics concerning the rectal sample. In some implementations, the user device and/or the analyzing platform determines, based on the first set of visual characteristics and the second set of visual characteristics, rectal sample information. For example, the user device and/or the analyzing platform may determine one or more estimated biochemical measurements associated with the rectal sample, a turbidity score of the rectal sample, information concerning estimated bowel cleanliness of the bowel of the user, and/or the like. In some implementations, the user device and/or the analyzing platform causes, based on the rectal sample information, one or more actions to be performed, such as scheduling a time for a colonoscopy, a physical examination, a blood test, and/or the like; causing display on a display of the user device of an instruction regarding consumption of a bowel preparation agent by the user; and/or the like.

In this way, the user device and/or the analyzing platform mitigates unnecessary use of resources associated with scheduling and performing the colonoscopy. For example, the user device and/or the analyzing platform may increase a likelihood that the quality of bowel preparation of the user is good, which increases a likelihood that the endoscopist can visualize colonic mucosa in the user's colon and identify abnormal findings. This increases a likelihood that a colonoscopy will be successfully performed without having to perform another colonoscopy on the user prematurely. Accordingly, device resources (e.g., processing resources, memory resources, power resources, communication resources, and/or the like) will not be consumed to schedule another colonoscopy. Further, imaging resources (e.g., processing resources, memory resources, power resources, communication resources, and/or the like) and cleaning and sterilizing resources will not be wasted on a colonoscopy that needs to be redone.

Further, the user device and/or the analyzing platform, based on the one or more biochemical measurements, may be able to determine an estimated health condition of the user (e.g., that indicates whether the user has a gastrointestinal disease, whether the user is at risk of developing a gastrointestinal disease, whether the user is anemic, whether the user is dehydrated, and/or the like), which may assist in determining a course of treatment for the user. Accordingly, resources, such as device resources for scheduling tests, analyzing test results, and/or the like, that would have been used to otherwise determine the estimated health condition of the user can be conserved.

FIGS. 1A-1D are diagrams of example implementations 100 described herein. As shown in FIG. 1A, example implementation 100 may include a user device and/or an analyzing platform. The user device may be a communication and/or computing device, such as a mobile phone, a smartphone, a laptop computer, a tablet computer, a smart toilet seat (e.g., a toilet seat device with capabilities to obtain and/or analyze images of rectal samples, as described herein), and/or the like. In some implementations, the user device may include a camera device (e.g., one or more cameras) configured to capture images. In some implementations, the camera device of the user device may support one or more image resolutions. An image resolution may be represented as a number of pixel columns (width) and a number of pixel rows (height), such as 1280×720, 1920×1080, 2592×1458, 3840×2160, 4128×2322, 5248×2952, 5312×2988, and/or the like, where higher numbers of pixel columns and higher numbers of pixel rows are associated with higher image resolutions. In some implementations, the user device may include one or more applications (e.g., provided by, or associated with, an entity, such as a health care provider (e.g., a hospital, a doctor's group, and/or the like)) capable of facilitating image capturing. In some implementations, a user of the user device may activate the one or more applications on the user device (e.g., cause the one or more applications to run on the user device) to capture an image.

In some implementations, the camera device may be configured to capture hyperspectral images (e.g., images associated with infrared light, visible light, ultraviolet, and/or the like). In some implementations, the camera device may include a filter (e.g., a bandpass filter) that is configured to allow the camera device to capture images associated with a particular spectral range (e.g., images associated with red light, green light, blue light, visible light, infrared light, ultraviolet light, and/or the like). Additionally, or alternatively, the user device may be configured to filter images obtained by the camera device (e.g., using the one or more applications) to allow the user device to modify the images (e.g., to cause the images to include only image data associated with a particular spectral range).

The analyzing platform may be a computing device, a server device, a cloud computing device, and/or the like. In some implementations, the user device and/or the analyzing platform may be connected via a network, such as a wired network (e.g., the Internet or another data network), a wireless network (e.g., a wireless local area network, a wireless wide area network, a cellular network, etc.), and/or the like.

Some example implementations described herein concern a single user device communicating with a single analyzing platform. In some implementations, a plurality of user devices may communicate with one or more analyzing platforms. In some implementations, one or more functions of the analyzing platform may be performed by the user device instead of, or in addition to, being performed by the analyzing platform. In some implementations, one or more functions of the user device may be performed by the analyzing platform instead of, or in addition to, being performed by the user device.

As shown by reference number 102, the user device may obtain user information relating to the user (e.g., a subject whose rectal sample will be analyzed, as described herein). For example, the user may interact, via a user interface of the user device, with the one or more applications running on the user device to enter the user information into the user device. As another example, the user device may communicate with a different device, such as a server device, to obtain the user information. The user information may include an age of the user, a sex of the user, a health status of the user, a health history of the user, information concerning medication consumed by the user, information concerning a bowel preparation agent prescribed for the user (e.g., to cleanse the bowel of the user for a bowel screening procedure for the user), information concerning the bowel screening procedure for the user (e.g., a timing of the bowel screening procedure), and/or the like.

As shown by reference number 104, in some implementations, when the user has consumed a bowel preparation agent in anticipation of a bowel screening procedure (e.g., a colonoscopy, a virtual colonoscopy, a flexible sigmoidoscopy, and/or the like), the user device may obtain consumption information concerning consumption of the bowel preparation agent by the user. For example, the user may interact, via the user interface of the user device, with the one or more applications running on the user device to enter the consumption information into the user device. As another example, the user device may communicate with a different device, such as a server device, to obtain the consumption information. The consumption information may include information concerning a dosage of the bowel preparation agent, information concerning an amount of bowel preparation agent consumed by the user, information concerning an amount of time since the amount of bowel preparation agent was consumed by the user, information concerning a total amount of bowel preparation agent consumed by the user, information concerning a time of an initial consumption of the bowel preparation agent by the user, and/or the like.

As shown by reference number 106, the user device may send the user information and/or the consumption information to the analyzing platform. In some implementations, the analyzing platform may obtain the user information and/or the consumption information from the user device. Additionally, or alternatively, the analyzing platform may communicate with a different device, such as a server device, to obtain the user information and/or the consumption information.

Figure 1B:
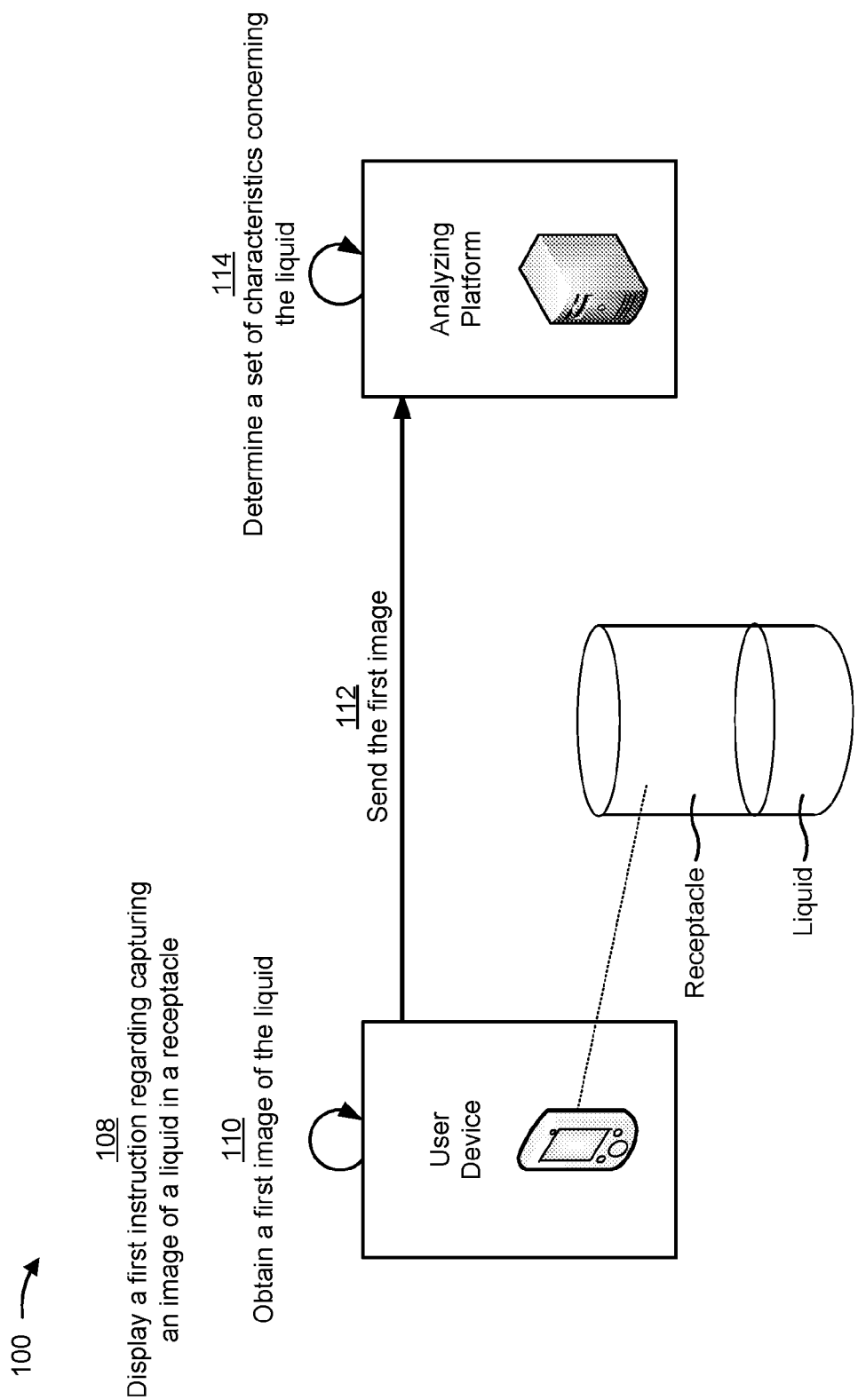

As shown in FIG. 1B and by reference number 108, the user device (e.g., via the one or more applications running on the user device) may display, on a display of the user device, a first instruction regarding capturing an image of a liquid in a receptacle. For example, the one or more applications may instruct a user to position the user device over the receptacle for the user device to capture an image of the liquid in the receptacle. In some implementations, the receptacle may be a container, such as a bottle, a sample tube, and/or the like. Additionally, or alternatively, the receptacle may be a toilet, a bedpan, and/or the like. The liquid may be water (e.g., water in a toilet), a chemical solution (e.g., a saline solution, a deodorizing solution, a solution with a colored dye, and/or the like), and/or the like.

As shown by reference number 110, the user device may obtain a first image of the liquid in the receptacle. In some implementations, the user may point the camera device of the user device at the liquid in the receptacle and/or the camera device of the user device may automatically capture the first image. Additionally, or alternatively, the user may point the camera device of the user device at the liquid and/or the user may interact, via the user interface of the user device, with the one or more applications running on the user device (e.g., to select an option to capture an image) to cause the camera device to capture the first image. The first image may include image data associated with a particular spectral range (e.g., an image associated with red light, green light, blue light, visible light, infrared light, ultraviolet light, and/or the like). The user device may cause the display of the user device to display the first image after the user device captures the first image. As shown by reference number 112, the user device may send the first image to the analyzing platform. In some implementations, the analyzing platform may obtain the first image from the user device.

As shown by reference number 114, the analyzing platform may determine a set of characteristics (e.g., visual characteristics) concerning the liquid. The set of characteristics may include a color associated with the liquid; a light intensity associated with the liquid; a brightness associated with the liquid; a spectral feature (e.g., a visible spectral feature, a near-infrared spectral feature, and/or the like), a biochemical feature, a molecular feature, and/or the like of the liquid, and/or the like. In some implementations, the analyzing platform may analyze and/or process (e.g., using one or more image analyzing techniques and/or one or more image processing techniques) the first image to determine the set of characteristics. For example, the analyzing platform may determine a color associated with the liquid by processing the first image using a color normalization technique. The analyzing platform may analyze the first image, after color normalizing the first image, to determine a light intensity associated with the liquid, a brightness associated with the liquid, and/or the like. In some implementations, the analyzing platform may determine an area of the first image associated with the liquid (e.g., using an object recognition technique) and may analyze and/or process image data of the first image associated with the area (e.g., only analyze and/or process image data associated with the area and not image data associated with the rest of the first image) to determine the set of characteristics.

In some implementations, the user, after the user device obtains the first image, may deposit a rectal sample (e.g., rectal effluent, rectal discharge, stool, and/or the like) in the liquid in the receptacle (e.g., the user may evacuate the rectal sample from the bowel of the user into the receptacle). In some implementations, the rectal sample may be diluted in the receptacle (e.g., the rectal sample may be mixed with the liquid in the receptacle, such as water in a toilet). In some implementations, the user, the user device, another device, and/or the like may deposit a reagent (e.g., a reactant, a solvent, a catalyst, and/or the like) in the receptacle with the rectal sample (e.g., to cause a chemical reaction associated with the rectal sample).

Figure 1C:
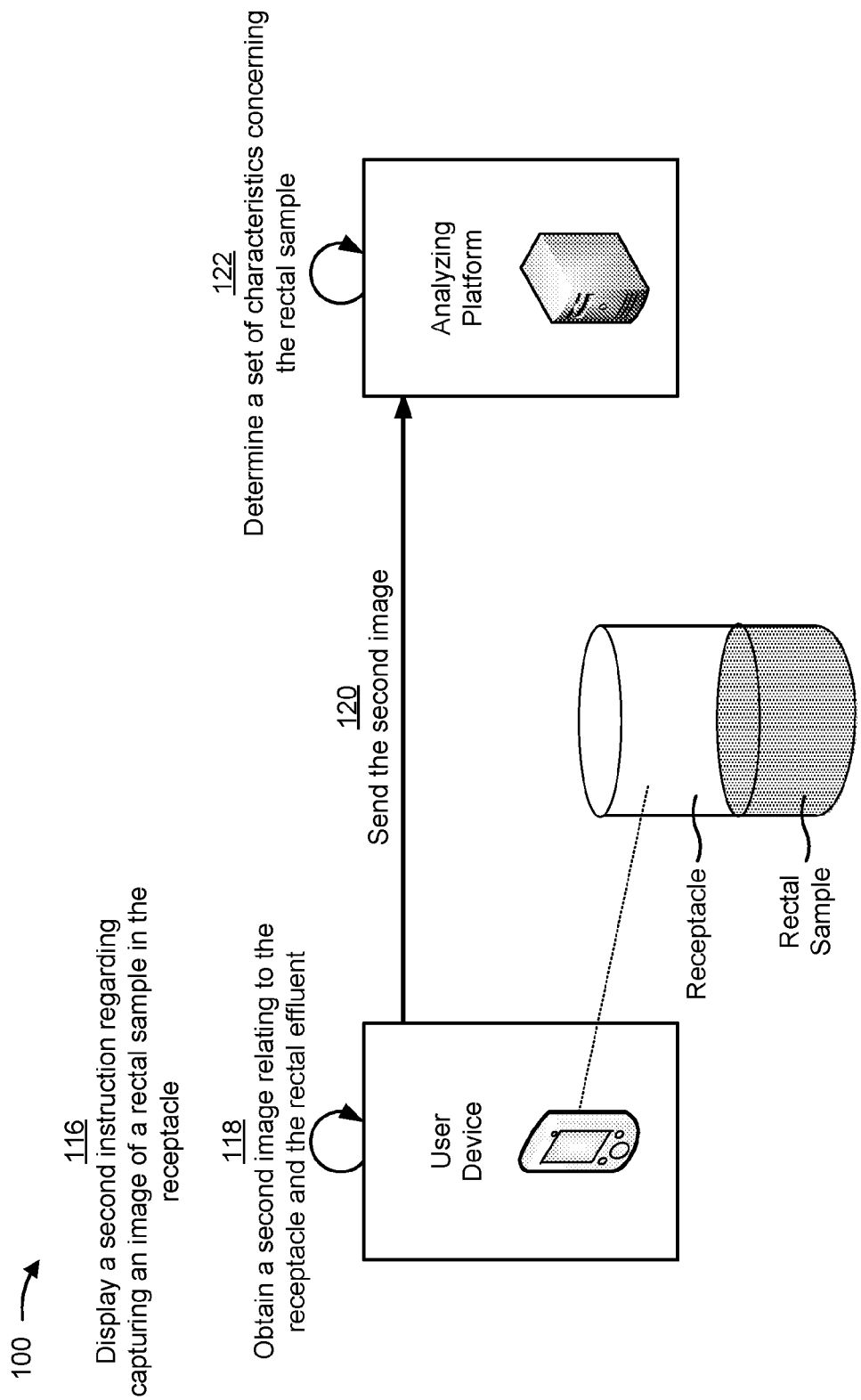

As shown in FIG. 1C and by reference number 116, the user device (e.g., via the one or more applications running on the user device) may display a second instruction regarding capturing an image of the rectal sample (e.g., of the user) in the liquid in the receptacle in a similar manner as described herein in relation to FIG. 1B. For example, the one or more applications may instruct the user to position the user device over the receptacle for the user device to capture an image of the rectal sample in the liquid in the receptacle.

As shown by reference number 118, the user device may obtain a second image of the rectal sample in the receptacle in a similar manner as described herein in relation to FIG. 1B. For example, the user may point the camera device of the user device at the rectal sample in the liquid in the receptacle and/or the camera device of the user device may automatically capture the second image. Additionally, or alternatively, the user may point the camera device of the user device at the rectal sample and/or the user may interact, via the user interface of the user device, with the one or more applications running on the user device (e.g., to select an option to capture an image) to cause the camera device to capture the second image. The user device may cause the display of the user device to display the second image after the user device captures the second image. The second image may include image data associated with a particular spectral range (e.g., an image associated with red light, green light, blue light, visible light, infrared light, ultraviolet light, and/or the like). The user device may cause the display of the user device to display the second image after the user device captures the second image.

As shown by reference number 120, the user device may send the second image to the analyzing platform in a similar manner as described herein in relation to FIG. 1B. In some implementations, the analyzing platform may obtain the second image from the user device.

As shown by reference number 122, the analyzing platform may determine a set of characteristics (e.g., visual characteristics) concerning the rectal sample in a similar manner as described herein in relation to FIG. 1B. The set of characteristics may include a color associated with the rectal sample; a light intensity associated with the rectal sample; a brightness associated with the rectal sample; a spectral feature (e.g., a visible spectral feature, a near-infrared spectral feature, and/or the like), a biochemical feature, a molecular feature, and/or the like of the liquid; a shape of the rectal sample; and/or the like. In some implementations, the analyzing platform may analyze and/or process (e.g., using one or more image analyzing techniques and/or one or more image processing techniques) the second image to determine the set of characteristics. For example, the analyzing platform may determine a color associated with the rectal sample by processing the second image using a color normalization technique. The analyzing platform may analyze the second image, after color normalizing the second image, to determine a light intensity associated with the rectal sample, a brightness associated with the rectal sample, and/or the like. In some implementations, the analyzing platform may determine an area of the second image associated with the rectal sample (e.g., using an object recognition technique) and may analyze and/or process image data of the second image associated with the area (e.g., only process image data associated with the area and not image data associated with the rest of the first image) to determine the set of characteristics.

Figure 1D:
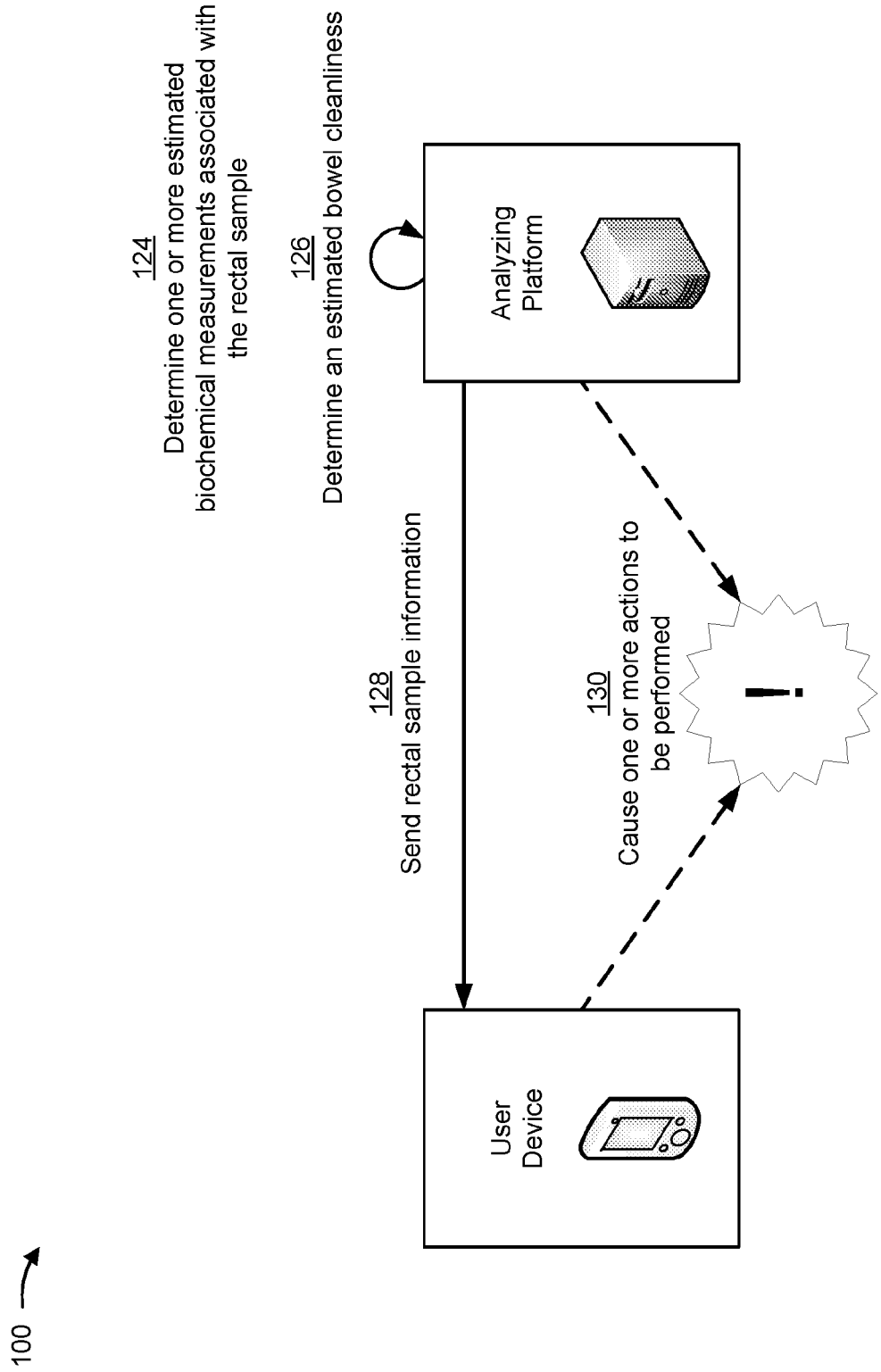

As shown in FIG. 1D and by reference number 124, the analyzing platform may determine one or more estimated biochemical measurements associated with the rectal sample. The one or more biochemical measurements may include an estimated hemoglobin measurement associated with the rectal sample (e.g., an estimated amount of hemoglobin in the rectal sample); an estimated protein measurement associated with the rectal sample (e.g., an estimated amount of protein in the rectal sample); an estimated fat measurement associated with the rectal sample (e.g., an estimated amount of fat in the rectal sample); an estimated carbohydrate measurement associated with the rectal sample (e.g., an estimated amount of carbohydrate in the rectal sample); an estimated nucleic acid measurement associated with the rectal sample (e.g., an estimated amount of nucleic acid in the rectal sample); an estimated acidity measurement associated with the rectal sample (e.g., an estimated pH value of the rectal sample); and/or the like.

In some implementations, the analyzing platform may determine the one or more estimated biochemical measurements associated with the rectal sample based on the set of characteristics of the liquid (hereinafter the "first set of characteristics") and/or the set of characteristics of the rectal sample (hereinafter the "second set of characteristics"). In some implementations, the analyzing platform may compare one or more elements of the first set of characteristics (e.g., the color associated with the liquid, light intensity associated with the liquid, the brightness associated with the liquid, and/or the like) and corresponding one or more elements of the second set of characteristics (e.g., the color associated with the rectal sample, the light intensity associated with the rectal sample, the brightness associated with the rectal sample, and/or the like) to determine the one or more estimated biochemical measurements. For example, the analyzing platform may compare the color associated with the liquid and the color associated with the rectal sample and/or may use a colorimetric processing technique to determine the one or more estimated biochemical measurements.

In some implementations, the analyzing platform may utilize one or more first models (e.g., one or more machine learning models) to process and/or analyze the first set of characteristics and/or the second set of characteristics to determine the one or more estimated biochemical measurements associated with the rectal sample. The analyzing platform may train a first model (e.g., one of the one or more first models, each of the one or more first models, and/or the like) based on historical data (e.g., historical information concerning first sets of characteristics, historical information concerning second sets of characteristics, historical information concerning estimated biochemical measurements, and/or the like). The analyzing platform may separate the historical data into a training set, a validation set, a test set, and/or the like. The training set may be utilized to train the first model. The validation set may be utilized to validate results of the trained first model. The test set may be utilized to test operation of the first model.

In some implementations, the analyzing platform may train the first model using, for example, an unsupervised training procedure and based on the historical data. For example, the analyzing platform may perform dimensionality reduction to reduce the historical data to a minimum feature set, thereby reducing resources (e.g., processing resources, memory resources, and/or the like) to train the first model, and may apply a classification technique to the minimum feature set.

In some implementations, the analyzing platform may use a logistic regression classification technique to determine a categorical outcome. Additionally, or alternatively, the analyzing platform may use a naïve Bayesian classifier technique. In this case, the analyzing platform may perform binary recursive partitioning to split the historical data into partitions and/or branches and use the partitions and/or branches to determine outcomes. Based on using recursive partitioning, the analyzing platform may reduce utilization of computing resources relative to manual, linear sorting and analysis of data points, thereby enabling use of thousands, millions, or billions of data points to train the first model, which may result in a more accurate model than using fewer data points.

Additionally, or alternatively, the analyzing platform may use a support vector machine (SVM) classifier technique to generate a non-linear boundary between data points in the training set. In this case, the non-linear boundary is used to classify test data into a particular class.

Additionally, or alternatively, the analyzing platform may train the first model using a supervised training procedure that includes receiving input to the first model from a subject matter expert, which may reduce an amount of time, an amount of processing resources, and/or the like to train the first model relative to an unsupervised training procedure. The analyzing platform may use one or more other model training techniques, such as a neural network technique, a latent semantic indexing technique, and/or the like. For example, the analyzing platform may perform an artificial neural network processing technique (e.g., using a two-layer feedforward neural network architecture, a three-layer feedforward neural network architecture, and/or the like) to perform pattern recognition with regard to patterns of the historical data. In this case, using the artificial neural network processing technique may improve an accuracy of the trained first model generated by the analyzing platform by being more robust to noisy, imprecise, or incomplete data, and by enabling the analyzing platform to detect patterns and/or trends undetectable to human analysts or systems using less complex techniques.

In some implementations, rather than training the first model, the analyzing platform may receive a trained first model from another device (e.g., a server device). For example, the other device may generate the first model based on having trained the first model in a manner similar to that described above, and may provide the trained first model to the analyzing platform (e.g., may pre-load the analyzing platform with the trained first model, may receive a request from the analyzing platform for the first trained model, and/or the like).

Additionally, or alternatively, as shown by reference number 126, the analyzing platform may determine information concerning estimated bowel cleanliness of the user (e.g., to assist in determining whether a bowel of the user is sufficiently clean to undergo a bowel screening procedure). The information concerning estimated bowel cleanliness may indicate an estimated degree of bowel visualization (e.g., based on a bowel cleanliness rating scale, such as the Boston Bowel Preparation Scale (BBPS)). In some implementations, the analyzing platform may determine the information concerning estimated bowel cleanliness based on a turbidity score of the rectal sample (e.g., that includes rectal effluent). The turbidity score may indicate a measure of turbidity of the rectal sample (e.g., a relative clarity of the rectal sample). A high turbidity score may indicate that the rectal sample has high turbidity, a low turbidity score may indicate that the rectal sample has low turbidity, and/or the like.

In some implementations, the analyzing platform may determine the turbidity score based on the first set of characteristics and/or the second set of characteristics. The analyzing platform may compare one or more elements of the first set of characteristics (e.g., the color associated with the liquid, the light intensity associated with the liquid, the brightness associated with the liquid, and/or the like) and corresponding one or more elements of the second set of characteristics (e.g., the color associated with the rectal sample, the light intensity associated with the rectal sample, the brightness associated with the rectal sample, and/or the like) to determine the turbidity score. For example, the analyzing platform may compare the light intensity associated with the liquid (e.g., after color normalizing the first image) and the light intensity associated with the rectal sample (e.g., after color normalizing the second image) to determine a light intensity value (e.g., a difference in the light intensity associated with the liquid and the light intensity associated with the rectal sample). The analyzing platform may determine the turbidity score based on the light intensity value (e.g., based on a known relationship, such a linear relationship, an exponential relationship, an inverse relationship, and/or the like, between turbidity scores and light intensity values).

In some implementations, the analyzing platform may utilize one or more second models (e.g., one or more machine learning models) to process and/or analyze the first set of characteristics and/or the second set of characteristics to determine the turbidity score. In some implementations, the analyzing platform may receive, generate, and/or train the second model in a similar manner as described herein in relation to the first model. For example, the analyzing platform may train a second model (e.g., one of the one or more second models, each of the one or more second models, and/or the like) based on historical data (e.g., historical information concerning first sets of characteristics, historical information concerning second sets of characteristics, historical information concerning turbidity scores, and/or the like). In some implementations, the analyzing platform may perform a set of data manipulation procedures, perform a training operation, use a classification technique, perform a recursive feature elimination procedure, and/or the like as described herein to determine an association between a first set of characteristics, a second set of characteristics, and/or a turbidity score.

In some implementations, the analyzing platform may determine the information concerning estimated bowel cleanliness based on the turbidity score of the rectal sample, as well as the user information, the consumption information, and/or the like. For example, the analyzing platform may determine the information concerning estimated bowel cleanliness based on the age of the user, the health status of the user, the information concerning the amount of bowel preparation agent consumed by the user, the information concerning the time of consumption of the amount of bowel preparation agent consumed by the user, and/or the turbidity score.

In some implementations, the analyzing platform may utilize one or more third models (e.g., one or more machine learning models) to process and/or analyze the user information, the consumption information, the turbidity score, and/or the like to determine the information concerning estimated bowel cleanliness. In some implementations, the analyzing platform may receive, generate, and/or train a third model in a similar manner as described herein in relation to the first model and/or the second model. For example, the analyzing platform may train a third model (e.g., one of the one or more third models, each of the one or more third models, and/or the like) based on historical data (e.g., historical user information, historical consumption information, historical turbidity scores, and/or the like). In some implementations, the analyzing platform may perform a set of data manipulation procedures, perform a training operation, use a classification technique, perform a recursive feature elimination procedure, and/or the like as described herein to determine an association between user information, consumption information, a turbidity score, and/or information concerning estimated bowel cleanliness.

As shown by reference number 128, the analyzing platform may send rectal sample information to the user device. The rectal sample information may include the one or more estimated biochemical measurements associated with the rectal sample, the turbidity score, the information concerning estimated bowel cleanliness, and/or the like. In some implementations, the user device may obtain the rectal sample information from the analyzing platform.

As shown by reference number 130, the analyzing platform and/or the user device may cause one or more actions. For example, the user device and/or the analyzing platform may cause at least one estimated biochemical measurement, of the one or more estimated biochemical measurements associated with the rectal sample, to be displayed on a display of the user device.

As another example, the user device and/or analyzing platform may determine that an estimated biochemical measurement is outside a normal range (e.g., the estimated biochemical measurement is less than a normal minimum measurement or greater than a normal maximum measurement). The user device and/or the analyzing platform may determine, based on determining that the estimated biochemical measure is outside the normal range, an estimated health condition of the user (e.g., that indicates whether the user has a gastrointestinal disease, whether the user is at risk of developing a gastrointestinal disease, whether the user is anemic, whether the user is dehydrated, and/or the like). The user device and/or the analyzing platform may cause, based on the estimated health condition of the user, a different device, such as a server device, to schedule an appointment time for a bowel screening procedure, a blood test, a physical examination (e.g., by a doctor), and/or the like.

In another example, the analyzing platform may receive information concerning one or more biochemical measurements from a different device (e.g., a laboratory technician may send, using the different device, information concerning blood test results of the user to the analyzing platform). The analyzing platform may cause the first model to be updated based on the first image, the second image, the user information, the one or more estimated biochemical measurement, and/or the information concerning one or more biochemical measurements.

In an additional example, the user device, based on the turbidity score and/or the information concerning estimated bowel cleanliness, may generate one or more instructions concerning consumption of a bowel preparation agent (e.g., for a bowel screening procedure) by the user and cause the user device to display the one or more instructions on the display of the user device. The one or more instructions may indicate that the user is to stop consuming the bowel preparation agent, that the user is to take a particular amount of the bowel preparation agent at a particular time, that the user is to contact a medical professional (e.g., a doctor, a nurse, and/or the like) about consumption of the bowel preparation agent, and/or the like. In another example, the user device may determine a dose of the bowel preparation agent to be consumed by the user, determine a time the dose is to be consumed by the user, and cause the user device to display information concerning the dose and the time on a display of the user device.

In an additional example, the user device and/or the analyzing platform may determine a time range for commencing a bowel screening procedure for the user based on the user information, the consumption information, the one or more estimated biochemical measurements associated with the rectal sample, the turbidity score, and/or the information concerning estimated bowel cleanliness of the user. The user device may generate a message that includes the time range and send the message to a different device, such as a server device, to cause the different device to schedule an appointment time concerning the bowel screening procedure. In this way, the user device and/or the analyzing platform can facilitate the bowel screening procedure occurring at a time when the bowel has a high likelihood of being clean and/or being visualized. In a different example, the user device may initiate a communication session with a communication device associated with a bowel screening procedure for the user (e.g., the user device may automatically call a communication device associated with a healthcare facility associated with the bowel screen procedure) to allow the user of the user device to communicate with a representative to schedule an appointment time concerning the bowel screening procedure.

In another example, the analyzing platform may receive information concerning turbidity of effluent in the bowel of the user from a different device (e.g., an endoscopist may collect and analyze effluent from the bowel of the user during the bowel screening procedure and send, using the different device, information concerning turbidity of the effluent to the analyzing platform). The analyzing platform may cause the second model to be updated based on the first image, the second image, the user information, the consumption information, the turbidity score, and/or the information concerning turbidity of effluent in the bowel of the user. In an additional example, the user device may receive information concerning actual bowel cleanliness of the user from a different device (e.g., an endoscopist may grade the cleanliness of the bowel of the user during the bowel screening procedure and send, using the different device, information concerning actual bowel cleanliness of the user to the analyzing platform). The analyzing platform may cause the third model to be updated based on the first image, the second image, the user information, the consumption information, the turbidity score, the information concerning estimated bowel cleanliness of the user, and/or the information concerning actual bowel cleanliness of the user.

In an additional example, the analyzing platform may receive feedback from the user of the user device (e.g., the user may enter feedback into the user device after the bowel screening procedure, and/or the user may use another device to enter the feedback, and send the feedback to the analyzing platform). The feedback may concern the bowel preparation agent, consumption of the bowel preparation agent, the bowel screening procedure, and/or the like. The analyzing platform may cause the second model and/or the third model to be updated based on the feedback.

Some example implementations described herein concern the user device and/or the analyzing platform obtaining and analyzing a first image and a second image to determine rectal sample information. In practice, implementations include the user device and/or the analyzing platform obtaining and analyzing multiple images, in a similar manner as described herein, to determine the rectal sample information.

Some example implementations described herein concern the analyzing platform performing one or more functions (e.g., determining the set of characteristics concerning the liquid, determining the set of characteristics concerning the rectal sample, determining the one or more estimated biochemical measurements associated with the rectal sample, determining the turbidity score, determining the information concerning estimated bowel cleanliness of the user, causing the one or more actions to be performed, and/or the like), but some implementations include the user device performing at least one function of the one or more functions. For example, in some implementations, the user device may not communicate with the analyzing platform and may perform all of the one or more functions. Additionally, or alternatively, some example implementations described herein concern the user device performing one or more additional functions (e.g., obtaining the user information, obtaining the consumption information, generating and/or causing display of messages, causing the one or more actions to be performed, and/or the like), but some implementations include the analyzing platform performing at least one additional function of the one or more additional functions.

Some example implementations described herein concern the analyzing platform performing and/or the user device determining one or more estimated biochemical measurements associated with a rectal sample, determining a turbidity score associated with the rectal sample, and/or the like. However, contemplated implementations include the analyzing platform and/or the user device determining one or more estimated biochemical measurements associated with other bodily fluids (e.g., urine, sputum, mucus, and/or the like), determining a turbidity score associated with other bodily fluids, and/or the like. For example, a turbidity score associated with urine may indicate a measure of specific gravity of a user's urine. Further, the analyzing platform and/or the user device may determine, based on the one or more estimated biochemical measurements and/or the turbidity score associated with the urine, sputum, mucus, and/or the like, information concerning an estimated indicator of health of the user. For example, the analyzing platform and/or user device may determine, based on the one or more estimated biochemical measurements and/or the turbidity score associated with the urine, information concerning an estimated hydration status of the user and/or information concerning estimated kidney function of the user in a similar manner as described herein.

As indicated above, FIGS. 1A-1D are provided merely as examples. Other examples may differ from what is described with regard to FIGS. 1A-1D.

Figure 2:
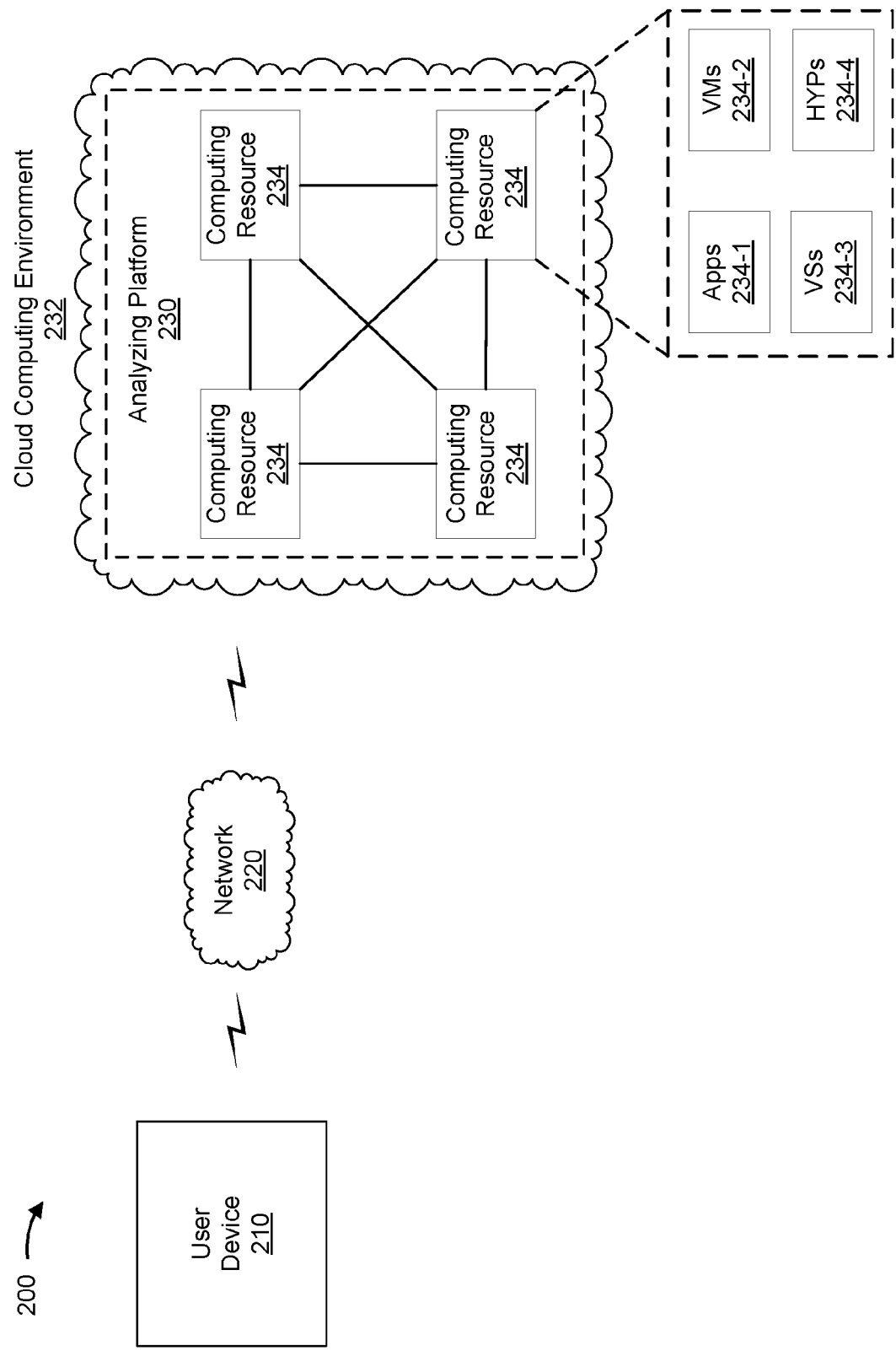
FIG. 2 is a diagram of an example environment in which systems and/or methods, described herein, may be implemented.

FIG. 2 is a diagram of an example environment 200 in which systems and/or methods described herein may be implemented. As shown in FIG. 2, environment 200 may include a user device 210, a network 220, an analyzing platform 230 in a cloud computing environment 232 that includes computing resources 234, and/or the like. Devices of environment 200 may interconnect via wired connections, wireless connections, or a combination of wired and wireless connections.

User device 210 includes one or more devices capable of receiving, generating, storing, processing, analyzing, and/or providing information, such as information described herein. For example, user device 210 may include a computer (e.g., a desktop computer, a laptop computer, a tablet computer, a handheld computer, a server device, etc.), a mobile phone (e.g., a smart phone, a radiotelephone, etc.), an internet of things (IOT) device or smart appliance, or a similar device. User device 210 may include a camera device and may be configured to capture an image using the camera device. The camera device may be configured to capture hyperspectral images and may include a filter that is configured to allow the camera device to capture images associated with a particular spectral range. In some implementations, user device 210 may receive information from and/or transmit information to analyzing platform 230, and/or the like.

Network 220 includes one or more wired and/or wireless networks. For example, network 220 may include a cellular network (e.g., a long-term evolution (LTE) network, a code division multiple access (CDMA) network, a 3G network, a 4G network, a 5G network, another type of next generation network, etc.), a public land mobile network (PLMN), a local area network (LAN), a wide area network (WAN), a metropolitan area network (MAN), a telephone network (e.g., the Public Switched Telephone Network (PSTN)), a private network, an ad hoc network, an intranet, the internet, a fiber optic-based network, a cloud computing network, a mesh network and/or the like, and/or a combination of these or other types of networks.

Analyzing platform 230 includes one or more devices capable of determining one or more estimated biochemical measurements associated with a rectal sample, determining a turbidity score of the rectal sample, and/or determining information concerning estimated bowel cleanliness of a user. In some implementations, analyzing platform 230 may be designed to be modular such that certain software components may be swapped in or out depending on a particular need. As such, analyzing platform 230 may be easily and/or quickly reconfigured for different uses. In some implementations, analyzing platform 230 may receive information from and/or transmit information to user device 210, such as via network 220.

In some implementations, as shown, analyzing platform 230 may be hosted in a cloud computing environment 232. Notably, while implementations described herein describe analyzing platform 230 as being hosted in cloud computing environment 232, in some implementations, analyzing platform 230 may be non-cloud-based (i.e., may be implemented outside of a cloud computing environment) or may be partially cloud-based.

Cloud computing environment 232 includes an environment that hosts analyzing platform 230. Cloud computing environment 232 may provide computation, software, data access, storage, etc, services that do not require end-user knowledge of a physical location and configuration of system(s) and/or device(s) that hosts analyzing platform 230. As shown, cloud computing environment 232 may include a group of computing resources 234 (referred to collectively as "computing resources 234" and individually as "computing resource 234").

Computing resource 234 includes one or more personal computers, workstation computers, server devices, or other types of computation and/or communication devices. In some implementations, computing resource 234 may host analyzing platform 230. The cloud resources may include compute instances executing in computing resource 234, storage devices provided in computing resource 234, data transfer devices provided by computing resource 234, etc. In some implementations, computing resource 234 may communicate with other computing resources 234 via wired connections, wireless connections, or a combination of wired and wireless connections.

As further shown in FIG. 2, computing resource 234 includes a group of cloud resources, such as one or more applications ("APPs") 234-1, one or more virtual machines ("VMs") 234-2, virtualized storage ("VSs") 234-3, one or more hypervisors ("HYPs") 234-4, and/or the like.

Application 234-1 includes one or more software applications that may be provided to or accessed by user device 210. Application 234-1 may eliminate a need to install and execute the software applications on user device 210. For example, application 234-1 may include software associated with analyzing platform 230 and/or any other software capable of being provided via cloud computing environment 232. In some implementations, one application 234-1 may send/receive information to/from one or more other applications 234-1, via virtual machine 234-2.

Virtual machine 234-2 includes a software implementation of a machine (e.g., a computer) that executes programs like a physical machine. Virtual machine 234-2 may be either a system virtual machine or a process virtual machine, depending upon use and degree of correspondence to any real machine by virtual machine 234-2. A system virtual machine may provide a complete system platform that supports execution of a complete operating system ("OS"). A process virtual machine may execute a single program, and may support a single process. In some implementations, virtual machine 234-2 may execute on behalf of a user (e.g., a user of user device 210), and may manage infrastructure of cloud computing environment 232, such as data management, synchronization, or long-duration data transfers.

Virtualized storage 234-3 includes one or more storage systems and/or one or more devices that use virtualization techniques within the storage systems or devices of computing resource 234. In some implementations, within the context of a storage system, types of virtualizations may include block virtualization and file virtualization. Block virtualization may refer to abstraction (or separation) of logical storage from physical storage so that the storage system may be accessed without regard to physical storage or heterogeneous structure. The separation may permit administrators of the storage system flexibility in how the administrators manage storage for end users. File virtualization may eliminate dependencies between data accessed at a file level and a location where files are physically stored. This may enable optimization of storage use, server consolidation, and/or performance of non-disruptive file migrations.

Hypervisor 234-4 may provide hardware virtualization techniques that allow multiple operating systems (e.g., "guest operating systems") to execute concurrently on a host computer, such as computing resource 234. Hypervisor 234-4 may present a virtual operating platform to the guest operating systems, and may manage the execution of the guest operating systems. Multiple instances of a variety of operating systems may share virtualized hardware resources.

The number and arrangement of devices and networks shown in FIG. 2 are provided as one or more examples. In practice, there may be additional devices and/or networks, fewer devices and/or networks, different devices and/or networks, or differently arranged devices and/or networks than those shown in FIG. 2. Furthermore, two or more devices shown in FIG. 2 may be implemented within a single device, or a single device shown in FIG. 2 may be implemented as multiple, distributed devices. Additionally, or alternatively, a set of devices (e.g., one or more devices) of environment 200 may perform one or more functions described as being performed by another set of devices of environment 200.

Figure 3:
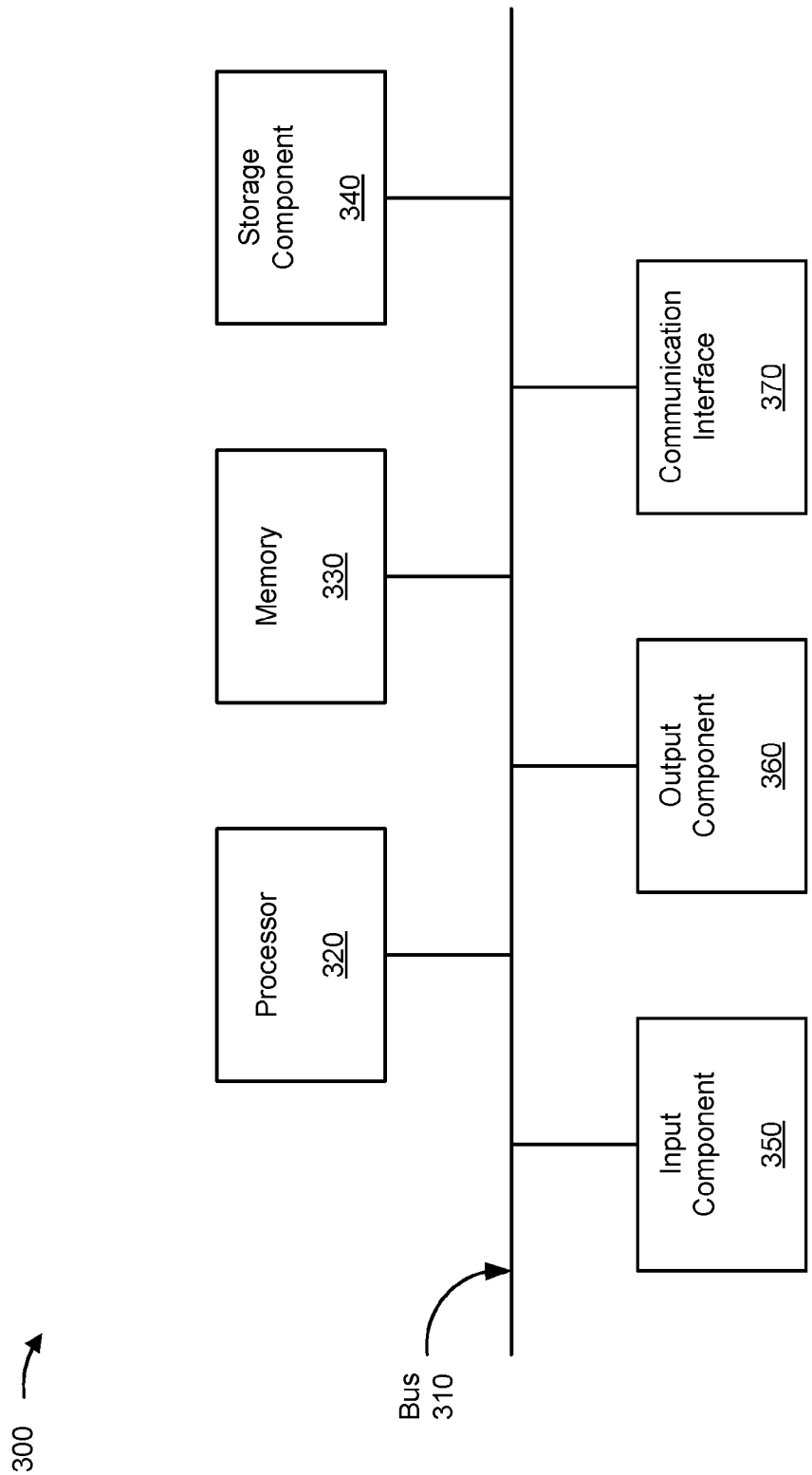
FIG. 3 is a diagram of example components of one or more devices of FIG. 2.

FIG. 3 is a diagram of example components of a device 300. Device 300 may correspond to user device 210, analyzing platform 230, computing resource 234, and/or the like. In some implementations, user device 210, analyzing platform 230, computing resource 234, and/or the like may include one or more devices 300 and/or one or more components of device 300. As shown in FIG. 3, device 300 may include a bus 310, a processor 320, a memory 330, a storage component 340, an input component 350, an output component 360, and a communication interface 370.

Bus 310 includes a component that permits communication among multiple components of device 300. Processor 320 is implemented in hardware, firmware, and/or a combination of hardware and software. Processor 320 is a central processing unit (CPU), a graphics processing unit (GPU), an accelerated processing unit (APU), a microprocessor, a microcontroller, a digital signal processor (DSP), a field-programmable gate array (FPGA), an application-specific integrated circuit (ASIC), or another type of processing component. In some implementations, processor 320 includes one or more processors capable of being programmed to perform a function. Memory 330 includes a random access memory (RAM), a read only memory (ROM), and/or another type of dynamic or static storage device (e.g., a flash memory, a magnetic memory, and/or an optical memory) that stores information and/or instructions for use by processor 320.

Storage component 340 stores information and/or software related to the operation and use of device 300. For example, storage component 340 may include a hard disk (e.g., a magnetic disk, an optical disk, and/or a magneto-optic disk), a solid state drive (SSD), a compact disc (CD), a digital versatile disc (DVD), a floppy disk, a cartridge, a magnetic tape, and/or another type of non-transitory computer-readable medium, along with a corresponding drive.

Input component 350 includes a component that permits device 300 to receive information, such as via user input (e.g., a touch screen display, a keyboard, a keypad, a mouse, a button, a switch, and/or a microphone). Additionally, or alternatively, input component 350 may include a component for determining location (e.g., a global positioning system (GPS) component) and/or a sensor (e.g., an accelerometer, a gyroscope, an actuator, another type of positional or environmental sensor, and/or the like). Output component 360 includes a component that provides output information from device 300 (via, e.g., a display, a speaker, a haptic feedback component, an audio or visual indicator, and/or the like).

Communication interface 370 includes a transceiver-like component (e.g., a transceiver, a separate receiver, a separate transmitter, and/or the like) that enables device 300 to communicate with other devices, such as via a wired connection, a wireless connection, or a combination of wired and wireless connections. Communication interface 370 may permit device 300 to receive information from another device and/or provide information to another device. For example, communication interface 370 may include an Ethernet interface, an optical interface, a coaxial interface, an infrared interface, a radio frequency (RF) interface, a universal serial bus (USB) interface, a Wi-Fi interface, a cellular network interface, and/or the like.

Device 300 may perform one or more processes described herein. Device 300 may perform these processes based on processor 320 executing software instructions stored by a non-transitory computer-readable medium, such as memory 330 and/or storage component 340. As used herein, the term "computer-readable medium" refers to a non-transitory memory device. A memory device includes memory space within a single physical storage device or memory space spread across multiple physical storage devices.

Software instructions may be read into memory 330 and/or storage component 340 from another computer-readable medium or from another device via communication interface 370. When executed, software instructions stored in memory 330 and/or storage component 340 may cause processor 320 to perform one or more processes described herein. Additionally, or alternatively, hardware circuitry may be used in place of or in combination with software instructions to perform one or more processes described herein. Thus, implementations described herein are not limited to any specific combination of hardware circuitry and software.

The number and arrangement of components shown in FIG. 3 are provided as an example. In practice, device 300 may include additional components, fewer components, different components, or differently arranged components than those shown in FIG. 3. Additionally, or alternatively, a set of components (e.g., one or more components) of device 300 may perform one or more functions described as being performed by another set of components of device 300.

Figure 4:
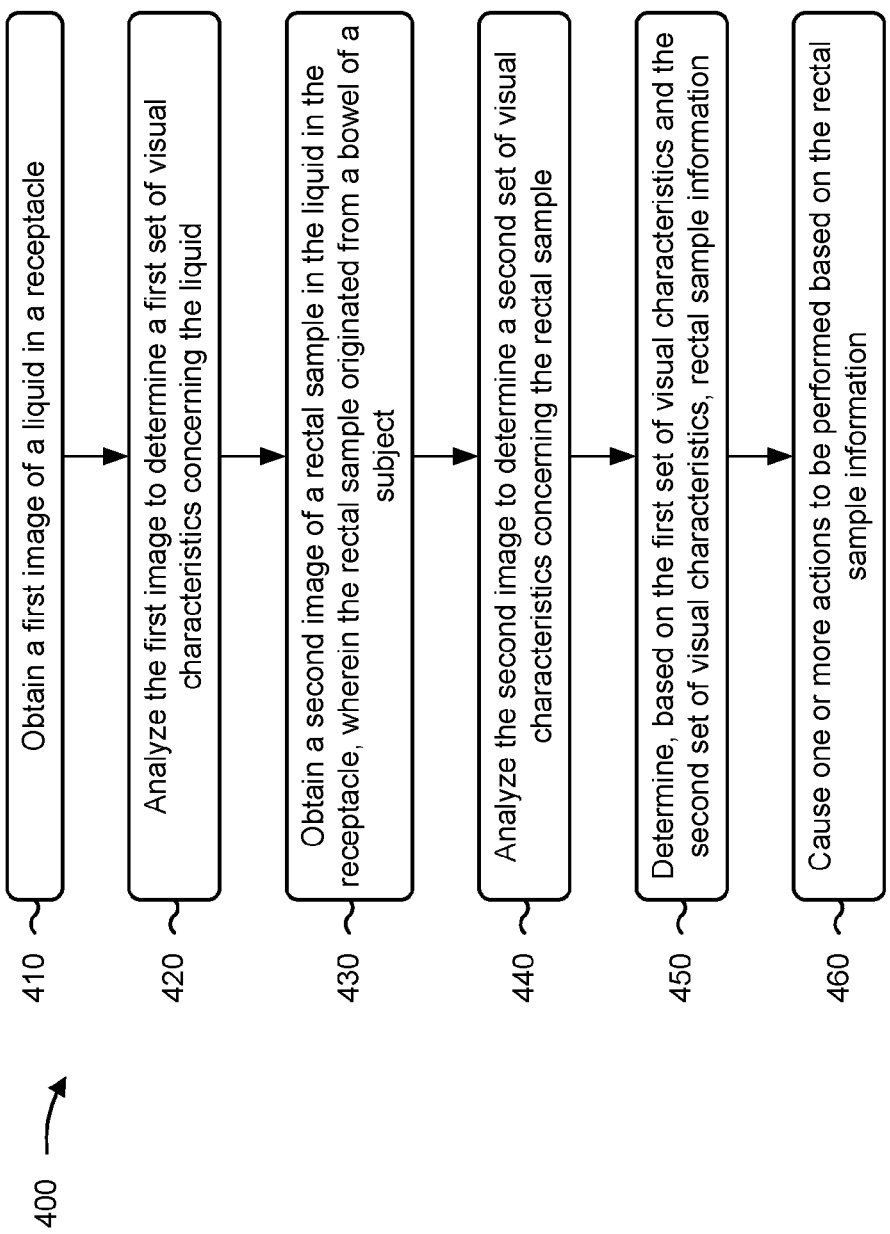

FIG. 4 is a flow chart of an example process 400 for analyzing image data to determine rectal sample information. In some implementations, one or more process blocks of FIG. 4 may be performed by a user device (e.g., user device 210). In some implementations, one or more process blocks of FIG. 4 may be performed by another device or a group of devices separate from or including the user device, such as analyzing platform 230, and/or the like.

As shown in FIG. 4, process 400 may include obtaining a first image of a liquid in a receptacle (block 410). For example, the user device (e.g., using processor 320, memory 330, storage component 340, input component 350, output component 360, communication interface 370 and/or the like) may obtain a first image of a liquid in a receptacle, as described above.

As further shown in FIG. 4, process 400 may include analyzing the first image to determine a first set of visual characteristics concerning the liquid (block 420). For example, the user device (e.g., using processor 320, memory 330, storage component 340, input component 350, output component 360, communication interface 370 and/or the like) may analyze the first image to determine a first set of visual characteristics concerning the liquid, as described above.

As further shown in FIG. 4, process 400 may include obtaining a second image of a rectal sample in the liquid in the receptacle, wherein the rectal sample originated from a bowel of a subject (block 430). For example, the user device (e.g., using processor 320, memory 330, storage component 340, input component 350, output component 360, communication interface 370 and/or the like) may obtain a second image of a rectal sample in the liquid in the receptacle, as described above. In some implementations, the rectal sample originated from a bowel of a subject.

As further shown in FIG. 4, process 400 may include analyzing the second image to determine a second set of visual characteristics concerning the rectal sample (block 440). For example, the user device (e.g., using processor 320, memory 330, storage component 340, input component 350, output component 360, communication interface 370 and/or the like) may analyze the second image to determine a second set of visual characteristics concerning the rectal sample, as described above.

As further shown in FIG. 4, process 400 may include determining, based on the first set of visual characteristics and the second set of visual characteristics, rectal sample information (block 450). For example, the user device (e.g., using processor 320, memory 330, storage component 340, input component 350, output component 360, communication interface 370 and/or the like) may determine, based on the first set of visual characteristics and the second set of visual characteristics, rectal sample information, as described above.

As further shown in FIG. 4, process 400 may include causing one or more actions to be performed based on the rectal sample information (block 460). For example, the user device (e.g., using processor 320, memory 330, storage component 340, input component 350, output component 360, communication interface 370 and/or the like) may cause one or more actions to be performed based on the rectal sample information, as described above.

Process 400 may include additional implementations, such as any single implementation or any combination of implementations described below and/or in connection with one or more other processes described elsewhere herein.

In a first implementation, the rectal sample information includes at least one of one or more estimated biochemical measurements associated with the rectal sample; a turbidity score of the rectal sample; or information concerning estimated bowel cleanliness of the bowel of the subject.

In a second implementation, alone or in combination with the first implementation, the one or more estimated biochemical measurements associated with the rectal sample include at least one of an estimated hemoglobin measurement associated with the rectal sample; an estimated protein measurement associated with the rectal sample; an estimated fat measurement associated with the rectal sample; an estimated carbohydrate measurement associated with the rectal sample; an estimated nucleic acid measurement associated with the rectal sample; or an estimated acidity measurement associated with the rectal sample.

In a third implementation, alone or in combination with one or more of the first and second implementations, analyzing the first image to determine the first set of visual characteristics further comprises determining a first area of the first image associated with the liquid, and analyzing image data of the first image associated with the first area to determine a light intensity and a color associated with the liquid, wherein analyzing the second image to determine the second set of visual characteristics further comprises determining a second area of the second image associated with the rectal sample in the liquid, and analyzing image data of the second image associated with the second area to determine a light intensity and a color associated with the rectal sample.

In a fourth implementation, alone or in combination with one or more of the first through third implementations, the rectal sample information includes information concerning estimated bowel cleanliness of the bowel of the subject, and determining the rectal sample information comprises determining, using at least one machine learning model and based on the first set of visual characteristics and the second set of visual characteristics, a turbidity score for the rectal sample that indicates a measure of turbidity of the rectal sample, and determining, using the at least one machine learning model and based on the turbidity score, the information concerning the estimated bowel cleanliness of the bowel of the subject.

In a fifth implementation, alone or in combination with one or more of the first through fourth implementations, the at least one machine learning model has been trained to determine the turbidity score based on a light intensity and a color associated with a particular liquid and a light intensity and a color associated with a particular rectal sample.

In a sixth implementation, alone or in combination with one or more of the first through fifth implementations, the additional machine learning model has been trained to determine the information concerning the estimated bowel cleanliness of the bowel of the subject based on at least one of: the turbidity score; an age of the subject; a sex of the subject; a health status of the subject; a health history of the subject; information concerning medication consumed by the subject; information concerning an amount of bowel preparation agent consumed by the subject; information concerning a dosage of the bowel preparation agent; information concerning an amount of time since the amount of bowel preparation agent was consumed by the subject; information concerning a total amount of bowel preparation agent consumed by the subject; or information concerning a time of an initial consumption of the bowel preparation agent by the subject.

In a seventh implementation, alone or in combination with one or more of the first through sixth implementations, determining the rectal sample information comprises: determining, using a machine learning model and based on the first set of visual characteristics and the second set of visual characteristics, one or more estimated biochemical measurements associated with the rectal sample.

In an eighth implementation, alone or in combination with one or more of the first through seventh implementations, the rectal sample information includes one or more estimated biochemical measurements associated with the rectal sample, and determining the rectal sample information comprises: determining, using a colorimetric processing technique and based on the first set of visual characteristics and the second set of visual characteristics, the one or more estimated biochemical measurements associated with the rectal sample.

In a ninth implementation, alone or in combination with one or more of the first through eighth implementations, causing the one or more actions to be performed comprises: generating one or more instructions concerning consumption of a bowel preparation agent by the subject, and causing a user device to display the one or more instructions on a display of the user device.

In a tenth implementation, alone or in combination with one or more of the first through ninth implementations, causing the one or more actions to be performed comprises: determining, based on the rectal sample information, a time range for commencing a bowel screening procedure for the subject; generating a message that includes the time range, and sending the message to a different device to cause the different device to schedule an appointment time concerning the bowel screening procedure.

Although FIG. 4 shows example blocks of process 400, in some implementations, process 400 may include additional blocks, fewer blocks, different blocks, or differently arranged blocks than those depicted in FIG. 4. Additionally, or alternatively, two or more of the blocks of process 400 may be performed in parallel.

Figure 5:
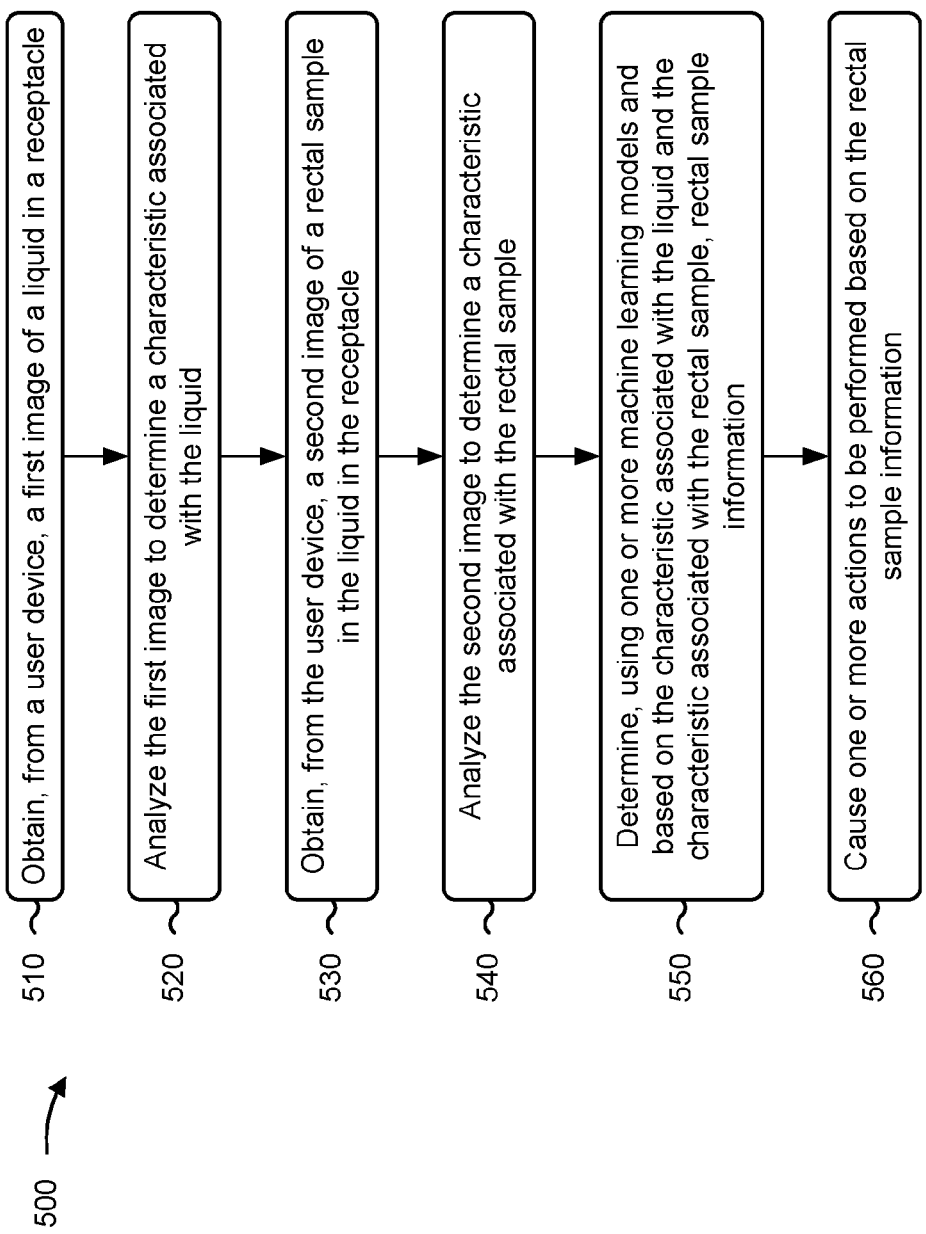

FIG. 5 is a flow chart of an example process 500 for analyzing image data to determine rectal sample information. In some implementations, one or more process blocks of FIG. 5 may be performed by an analyzing platform (e.g., analyzing platform 230). In some implementations, one or more process blocks of FIG. 5 may be performed by another device or a group of devices separate from or including the device, such as a user device (e.g., user device 210), and/or the like.

As shown in FIG. 5, process 500 may include obtaining, from a user device, a first image of a liquid in a receptacle (block 510). For example, the analyzing platform (e.g., using computing resource 234, processor 320, memory 330, storage component 340, input component 350, output component 360, communication interface 370 and/or the like) may obtain, from a user device, a first image of a liquid in a receptacle, as described above.

As further shown in FIG. 5, process 500 may include analyzing the first image to determine a characteristic associated with the liquid (block 520). For example, the analyzing platform (e.g., using computing resource 234, processor 320, memory 330, storage component 340, input component 350, output component 360, communication interface 370 and/or the like) may analyze the first image to determine a characteristic associated with the liquid, as described above.

As further shown in FIG. 5, process 500 may include obtaining, from the user device, a second image of a rectal sample in the liquid in the receptacle (block 530). For example, the analyzing platform (e.g., using computing resource 234, processor 320, memory 330, storage component 340, input component 350, output component 360, communication interface 370 and/or the like) may obtain, from the user device, a second image of a rectal sample in the liquid in the receptacle, as described above.

As further shown in FIG. 5, process 500 may include analyzing the second image to determine a characteristic associated with the rectal sample (block 540). For example, the analyzing platform (e.g., using computing resource 234, processor 320, memory 330, storage component 340, input component 350, output component 360, communication interface 370 and/or the like) may analyze the second image to determine a characteristic associated with the rectal sample, as described above.

As further shown in FIG. 5, process 500 may include determining, using one or more machine learning models and based on the characteristic associated with the liquid and the characteristic associated with the rectal sample, rectal sample information (block 550). For example, the analyzing platform (e.g., using computing resource 234, processor 320, memory 330, storage component 340, input component 350, output component 360, communication interface 370 and/or the like) may determine, using one or more machine learning models and based on the characteristic associated with the liquid and the characteristic associated with the rectal sample, rectal sample information, as described above.

As further shown in FIG. 5, process 500 may include causing one or more actions to be performed based on the rectal sample information (block 560). For example, the analyzing platform (e.g., using computing resource 234, processor 320, memory 330, storage component 340, input component 350, output component 360, communication interface 370 and/or the like) may cause one or more actions to be performed based on the rectal sample information, as described above.

Process 500 may include additional implementations, such as any single implementation or any combination of implementations described below and/or in connection with one or more other processes described elsewhere herein.

In a first implementation, the receptacle is a toilet and the liquid is water.

In a second implementation, alone or in combination with the first implementation, the characteristic associated with the liquid is a color associated with the liquid, a light intensity associated with the liquid, or a brightness associated with the liquid, and the characteristic associated with the rectal sample is a color associated with the rectal sample, a light intensity associated with the rectal sample, or a brightness associated with the rectal sample.

In a third implementation, alone or in combination with one or more of the first and second implementations, analyzing the first image to determine the characteristic associated with the liquid includes processing the first image to color normalize the first image; and determining the characteristic associated with the liquid after processing the first image, and analyzing the second image to determine the characteristic associated with the rectal sample includes processing the second image to color normalize the second image, and determining the characteristic associated with the rectal sample after processing the second image.

In a fourth implementation, alone or in combination with one or more of the first through third implementations, causing the one or more actions to be performed includes receiving additional rectal sample information from a different device; and causing at least one machine learning model, of the one or more machine learning models, to be updated based on the additional rectal sample information.

Although FIG. 5 shows example blocks of process 500, in some implementations, process 500 may include additional blocks, fewer blocks, different blocks, or differently arranged blocks than those depicted in FIG. 5. Additionally, or alternatively, two or more of the blocks of process 500 may be performed in parallel.

FIG. 6 is a flow chart of an example process 600 for analyzing image data to determine rectal sample information. In some implementations, one or more process blocks of FIG. 6 may be performed by a user device (e.g., user device 210). In some implementations, one or more process blocks of FIG. 6 may be performed by another device or a group of devices separate from or including the device, such as an analyzing platform (e.g., analyzing platform 230), and/or the like.

As shown in FIG. 6, process 600 may include causing display, on a display of the user device, of a first instruction regarding capturing an image of a liquid in a receptacle (block 610). For example, the user device (e.g., using processor 320, memory 330, storage component 340, input component 350, output component 360, communication interface 370 and/or the like) may cause display, on a display of the user device, of a first instruction regarding capturing an image of a liquid in a receptacle, as described above.

As further shown in FIG. 6, process 600 may include obtaining, after causing display of the first instruction, a first image of the liquid (block 620). For example, the user device (e.g., using processor 320, memory 330, storage component 340, input component 350, output component 360, communication interface 370 and/or the like) may obtain, after causing display of the first instruction, a first image of the liquid, as described above.

As further shown in FIG. 6, process 600 may include analyzing the first image to determine a first set of characteristics concerning the liquid (block 630). For example, the user device (e.g., using processor 320, memory 330, storage component 340, input component 350, output component 360, communication interface 370 and/or the like) may analyze the first image to determine a first set of characteristics concerning the liquid, as described above.

As further shown in FIG. 6, process 600 may include causing display, on the display of the user device, of a second instruction regarding capturing an image of a rectal sample, of a user of the user device, in the liquid in the receptacle (block 640). For example, the user device (e.g., using processor 320, memory 330, storage component 340, input component 350, output component 360, communication interface 370 and/or the like) may cause display, on the display of the user device, of a second instruction regarding capturing an image of a rectal sample, of a user of the user device, in the liquid in the receptacle, as described above.

As further shown in FIG. 6, process 600 may include obtaining, after causing display of the second instruction, a second image of the rectal sample (block 650). For example, the user device (e.g., using processor 320, memory 330, storage component 340, input component 350, output component 360, communication interface 370 and/or the like) may obtain, after causing display of the second instruction, a second image of the rectal sample, as described above.

As further shown in FIG. 6, process 600 may include analyzing the second image to determine a second set of characteristics concerning the rectal sample (block 660). For example, the user device (e.g., using processor 320, memory 330, storage component 340, input component 350, output component 360, communication interface 370 and/or the like) may analyze the second image to determine a second set of characteristics concerning the rectal sample, as described above.

As further shown in FIG. 6, process 600 may include determining, based on the first set of characteristics and the second set of characteristics, rectal sample information (block 670). For example, the user device (e.g., using processor 320, memory 330, storage component 340, input component 350, output component 360, communication interface 370 and/or the like) may determine, based on the first set of characteristics and the second set of characteristics, rectal sample information, as described above.

As further shown in FIG. 6, process 600 may include automatically performing one or more actions based on the rectal sample information (block 680). For example, the user device (e.g., using processor 320, memory 330, storage component 340, input component 350, output component 360, communication interface 370 and/or the like) may automatically perform one or more actions based on the rectal sample information, as described above.

Process 600 may include additional implementations, such as any single implementation or any combination of implementations described below and/or in connection with one or more other processes described elsewhere herein.

In a first implementation, a camera device of the user device is configured to obtain the first image of the liquid and the second image of the rectal sample, wherein the camera device is configured to capture hyperspectral images.

In a second implementation, alone or in combination with the first implementation, automatically performing the one or more actions includes initiating a communication session with a communication device associated with a bowel screening procedure for the user.

In a third implementation, alone or in combination with one or more of the first and second implementations, the rectal sample information includes one or more estimated biochemical measurements associated with the rectal sample, and automatically performing the one or more actions includes determining, based on the one or more estimated biochemical measurements associated with the rectal sample, an estimated health condition of the user, and automatically causing, based on the estimated health condition of the user, a different device to schedule an appointment time for at least one of the following: a bowel screening procedure, a blood test, or a physical examination of the user.

Although FIG. 6 shows example blocks of process 600, in some implementations, process 600 may include additional blocks, fewer blocks, different blocks, or differently arranged blocks than those depicted in FIG. 6. Additionally, or alternatively, two or more of the blocks of process 600 may be performed in parallel.

The foregoing disclosure provides illustration and description, but is not intended to be exhaustive or to limit the implementations to the precise forms disclosed. Modifications and variations may be made in light of the above disclosure or may be acquired from practice of the implementations.

As used herein, the term "component" is intended to be broadly construed as hardware, firmware, and/or a combination of hardware and software.

Certain user interfaces have been described herein and/or shown in the figures. A user interface may include a graphical user interface, a non-graphical user interface, a text-based user interface, and/or the like. A user interface may provide information for display. In some implementations, a user may interact with the information, such as by providing input via an input component of a device that provides the user interface for display. In some implementations, a user interface may be configurable by a device and/or a user (e.g., a user may change the size of the user interface, information provided via the user interface, a position of information provided via the user interface, etc.). Additionally, or alternatively, a user interface may be pre-configured to a standard configuration, a specific configuration based on a type of device on which the user interface is displayed, and/or a set of configurations based on capabilities and/or specifications associated with a device on which the user interface is displayed.

It will be apparent that systems and/or methods described herein may be implemented in different forms of hardware, firmware, or a combination of hardware and software. The actual specialized control hardware or software code used to implement these systems and/or methods is not limiting of the implementations. Thus, the operation and behavior of the systems and/or methods are described herein without reference to specific software code—it being understood that software and hardware can be designed to implement the systems and/or methods based on the description herein.

Even though particular combinations of features are recited in the claims and/or disclosed in the specification, these combinations are not intended to limit the disclosure of various implementations. In fact, many of these features may be combined in ways not specifically recited in the claims and/or disclosed in the specification. Although each dependent claim listed below may directly depend on only one claim, the disclosure of various implementations includes each dependent claim in combination with every other claim in the claim set.

No element, act, or instruction used herein should be construed as critical or essential unless explicitly described as such. Also, as used herein, the articles "a" and "an" are intended to include one or more items, and may be used interchangeably with "one or more." Furthermore, as used herein, the term "set" is intended to include one or more items (e.g., related items, unrelated items, a combination of related and unrelated items, etc.), and may be used interchangeably with "one or more." Where only one item is intended, the phrase "only one" or similar language is used. Also, as used herein, the terms "has," "have," "having," or the like are intended to be open-ended terms. Further, the phrase "based on" is intended to mean "based, at least in part, on" unless explicitly stated otherwise.

What is claimed is:

1. A device, comprising:
   one or more memories; and
   one or more processors, communicatively coupled to the one or more memories, configured to:
      obtain, before a rectal sample is deposited in a liquid in a receptacle, a first image of the liquid in the receptacle,
         wherein the rectal sample is associated with at least an animal or a human;
      analyze the first image to determine a first characteristic associated with the liquid in the receptacle;
      obtain a second image of the rectal sample in the liquid in the receptacle;
      analyze the second image to determine a second characteristic associated with the rectal sample;
      determine, based on the first characteristics and the second characteristic, one or more estimated biochemical measurements associated with the rectal sample; and
      cause one or more actions to be performed based on the one or more estimated biochemical measurements associated with the rectal sample.

2. The device of claim 1, wherein the one or more estimated biochemical measurements associated with the rectal sample includes at least one of:
   an estimated hemoglobin measurement associated with the rectal sample;
   an estimated protein measurement associated with the rectal sample;
   an estimated fat measurement associated with the rectal sample;
   an estimated carbohydrate measurement associated with the rectal sample;
   an estimated nucleic acid measurement associated with the rectal sample; or
   an estimated acidity measurement associated with the rectal sample.

3. The device of claim 1, wherein the one or more processors, when analyzing the second image to determine the second characteristic, are to:
   analyze image data associated with an area of the second image to determine the second characteristic.

4. The device of claim 1, wherein the second characteristic is a spectral feature associated with the rectal sample.

5. The device of claim 1, wherein the one or more processors, when determining the one or more estimated biochemical measurements associated with the rectal sample, are configured to:
   determine, using at least one machine learning model, and based on the first characteristic and the second characteristic, the one or more estimated biochemical measurements associated with the rectal sample.

6. The device of claim 1, wherein the one or more processors, when causing the one or more actions to be performed, are configured to:
   send the one or more estimated biochemical measurements associated with the rectal sample to a user device to cause the user device to display the one or more estimated biochemical measurements associated with the rectal sample on a display of the user device.

7. The device of claim 1, wherein the one or more processors, when causing the one or more actions to be performed, are configured to:
   determine, based on the one or more estimated biochemical measurements associated with the rectal sample, an estimated health condition of a subject associated with the rectal sample.

8. The device of claim 7, wherein the estimated health condition indicates at least one of:
   whether the subject has a gastrointestinal disease;
   whether the subject is at risk of developing a gastrointestinal disease;
   whether the subject is anemic; or
   whether the subject is dehydrated.

9. A non-transitory computer-readable medium storing instructions, the instructions comprising:
   one or more instructions that, when executed by one or more processors of a user device, cause the one or more processors to:
      obtain, before a bodily fluid is deposited in a liquid in a receptacle, a first image of the liquid in the receptacle,
         wherein the bodily fluid is associated with at least an animal or a human;
      analyze the first image to determine a first set of characteristics associated with the bodily fluid;
      obtain a second image of the bodily fluid in the liquid in the receptacle;
      analyze the second image to determine a second set of characteristics associated with the bodily fluid;
      determine, based on the first set of characteristics and the second set of characteristics, one or more estimated biochemical measurements associated with the bodily fluid; and
      cause one or more actions to be performed based on the one or more estimated biochemical measurements associated with the bodily fluid.

10. The non-transitory computer-readable medium of claim 9, wherein the bodily fluid includes at least one of:
   a rectal sample;
   urine;
   sputum; or
   mucus.

11. The non-transitory computer-readable medium of claim 9, wherein a camera device of the user device is configured to obtain the image of the bodily fluid,
   wherein the camera device is configured to capture hyperspectral images.

12. The non-transitory computer-readable medium of claim 9, wherein the second set of characteristics includes a spectral feature associated with the bodily fluid.

13. A method, comprising:
   obtaining, by a device and before a rectal sample is deposited in a liquid in a receptacle, a first image of the liquid in the receptacle,
      wherein the rectal sample is associated with at least an animal or a human;
   analyzing, by the device, the first image to determine a first set of characteristics concerning the liquid;
   obtaining, by the device, a second image of the rectal sample in the liquid in the receptacle,
      wherein the rectal sample originated from a bowel of a subject;
   analyzing, by the device, the second image to determine a second set of characteristics concerning the rectal sample;
   determining, by the device and based on the first set of characteristics and the second set of characteristics, an estimated hemoglobin measurement associated with the rectal sample; and
   causing, by the device, one or more actions to be performed based on the estimated hemoglobin measurement associated with the rectal sample.

14. The method of claim 13, wherein analyzing the first image to determine the first set of characteristics further comprises:
   determining a first area of the first image associated with the liquid; and
   analyzing image data of the first area to determine a spectral feature associated with the liquid,
      wherein analyzing the second image to determine the second set of characteristics further comprises:
         determining a second area of the second image associated with the rectal sample in the liquid, and
         analyzing image data of the second area to determine a spectral feature associated with the rectal sample.

15. The method of claim 13, wherein determining the estimated hemoglobin measurement associated with the rectal sample comprises:
   comparing, based on the first set of characteristics and the second set of characteristics, a spectral feature associated with the liquid and a spectral feature associated with the rectal sample to determine the estimated hemoglobin measurement associated with the rectal sample.

16. The method of claim 13, wherein determining the estimated hemoglobin measurement associated with the rectal sample comprises:
   determining, using a colorimetric processing technique and based on the first set of characteristics and the second set of characteristics, the estimated hemoglobin measurement associated with the rectal sample.

17. The method of claim 13, wherein determining the estimated hemoglobin measurement associated with the rectal sample comprises:
   determining, using at least one machine learning model and based on the first set of characteristics and the second set of characteristics, the estimated hemoglobin measurement associated with the rectal sample.

18. The method of claim 13, wherein causing the one or more actions to be performed comprises:
   causing a user device to display the estimated hemoglobin measurement associated with the rectal sample on a display of the user device.

19. The method of claim 13, wherein causing the one or more actions to be performed comprises:
   determining that the estimated hemoglobin measurement associated with the rectal sample is outside a particular range;
   determining, based on determining that the estimated hemoglobin measurement associated with the rectal sample is outside the particular range, an estimated health condition of the subject; and
   causing, based on the estimated health condition of the subject, a different device to schedule an appointment time for at least one of the following:
      a bowel screening procedure,
      a blood test, or
      a physical examination of the subject.

20. The method of claim 19, wherein the estimated health condition indicates whether the subject is anemic.

* * * * *